United States Patent
Nam et al.

(10) Patent No.: US 10,232,133 B2
(45) Date of Patent: Mar. 19, 2019

(54) APPARATUS FOR IMAGING

(71) Applicant: ELECTRONICS AND TELECOMMUNICATIONS RESEARCH INSTITUTE, Daejeon (KR)

(72) Inventors: Sae Kwang Nam, Daejeon (KR); Ki Uk Kyung, Daejeon (KR); Bong Je Park, Daejeon (KR); Sun Tak Park, Incheon (KR); Sung Ryul Yun, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 773 days.

(21) Appl. No.: 14/608,261

(22) Filed: Jan. 29, 2015

(65) Prior Publication Data
US 2015/0272428 A1    Oct. 1, 2015

(30) Foreign Application Priority Data

Mar. 28, 2014  (KR) .................. 10-2014-0036567
Nov. 7, 2014   (KR) .................. 10-2014-0154520

(51) Int. Cl.
*A61B 1/00* (2006.01)
*A61M 13/00* (2006.01)
(Continued)

(52) U.S. Cl.
CPC ......... *A61M 13/003* (2013.01); *A61B 1/0019* (2013.01); *A61B 1/00181* (2013.01);
(Continued)

(58) Field of Classification Search
CPC .............. A61B 1/00181; A61B 1/0019; A61B 1/00188; G02B 3/14; G02B 26/0875
(Continued)

(56) References Cited

U.S. PATENT DOCUMENTS 4,805,598 A * 2/1989 Ueda .................. A61B 1/00091
                                                  359/665
5,430,475 A * 7/1995 Goto ........................ A61B 1/05
                                                     348/65
(Continued)

FOREIGN PATENT DOCUMENTS

EP         1816491 A1    8/2007
KP    10-0949999 B1      3/2010

*Primary Examiner* — Timothy J Neal
*Assistant Examiner* — Jae Woo
(74) *Attorney, Agent, or Firm* — Rabin & Berdo, P.C.

(57) ABSTRACT

Provided herein is an endoscope comprising an end portion configured to take an image; a controller configured to control the end portion and process the image input by the end portion; and a connector configured to connect the end portion and the controller, wherein the end portion is provided with at least one lens apparatus surrounding an exterior surface of the end portion, the lens apparatus being adapted to be brought to various focuses, thereby providing an effect of obtaining images from various viewpoints at a short period of time, and when used as an endoscope, obviating the need to move the multi-view and multi-focused variable lens at the end portion, making it possible to reduce the thickness of the connector that connects the end portion of the endoscope with the controller.

15 Claims, 2 Drawing Sheets

(51) Int. Cl.
  *H04N 5/232*   (2006.01)
  *G02B 3/14*    (2006.01)
  *G02B 23/24*   (2006.01)
  *G02B 13/06*   (2006.01)
  *H04N 5/225*   (2006.01)

(52) U.S. Cl.
  CPC ............ *G02B 3/14* (2013.01); *G02B 23/243* (2013.01); *H04N 5/23212* (2013.01); *G02B 13/06* (2013.01); *H04N 2005/2255* (2013.01)

(58) Field of Classification Search
  USPC .................................................. 600/113, 176
  See application file for complete search history.

(56) References Cited

U.S. PATENT DOCUMENTS

| | | | |
|---|---|---|---|
| 5,547,455 A * | 8/1996 | McKenna | A61B 1/0005 348/65 |
| 6,319,196 B1 * | 11/2001 | Minami | A61B 1/05 348/76 |
| 7,428,114 B2 * | 9/2008 | Yu | G02B 15/14 359/819 |
| 7,545,430 B2 | 6/2009 | Nakagawa | |
| 9,091,810 B2 * | 7/2015 | Nam | G02B 3/14 |
| 2002/0128539 A1 * | 9/2002 | Higuma | A61B 1/00188 600/133 |
| 2010/0217076 A1 | 8/2010 | Ratnakar | |
| 2010/0286476 A1 * | 11/2010 | Jiang | A61B 1/00096 600/109 |
| 2010/0292535 A1 | 11/2010 | Paskar | |
| 2011/0038625 A1 * | 2/2011 | Zellers | G02B 7/04 396/133 |
| 2011/0261178 A1 * | 10/2011 | Lo | A61B 1/05 348/68 |
| 2012/0116158 A1 | 5/2012 | Hale et al. | |
| 2015/0065803 A1 * | 3/2015 | Douglas | A61B 1/00009 600/200 |
| 2015/0205096 A1 * | 7/2015 | Nam | G02B 3/14 359/291 |
| 2015/0223669 A1 * | 8/2015 | Goldfain | A61B 3/12 600/109 |
| 2015/0238071 A1 * | 8/2015 | Hua | A61B 1/07 600/109 |

* cited by examiner

APPARATUS FOR IMAGING

CROSS-REFERENCE TO RELATED APPLICATIONS

This application claims the benefit of priority under 35 U.S.C. § 119(a) of Korean Patent Application No. 10-2014-0036567, filed on Mar. 28, 2014 and No. 10-2014-0154520, filed on Nov. 7, 2014 in the Korean Intellectual Property Office, the entire disclosure of which is incorporated herein by reference for all purposes.

BACKGROUND

1. Field

The following description relates to an apparatus for imaging, and more particularly to an internal image apparatus or an endoscope.

The present disclosure was derived from researches conducted as part of an effort to develop active microlens array techniques capable of performing shape reconstruction on each lens.

2. Description of Related Art

An endoscope is a medical apparatus used for direct observation of internal organs or inside celoms. It has a camera at the end of a connecting portion capable of going in and out of organs and this record images, thereby helping doctors to look inside a celom and determine the state of illnesses.

Since the initial development of endoscopes, due to the development of new material called optical fiber in the 1960s, endoscopes have advanced significantly. Since then, soft optical endoscopes have been developed capable of directly observing inner walls of organs even when they are bent. Furthermore, it has become possible to perform endoscope operations effectively with images transmitted through optical fibers without the need of cameras.

People started to regard endoscope examination as an essential examination for early diagnosing of gastric cancer, and as sedated endoscopy became more widespread, people started to regard endoscope examination as causing less pain. Furthermore, thanks to the development of science and external environment based on promotion of national cancer examination projects, and internal environment based on the development of endoscopes that transcend physical and anatomical restraints, endoscope operations are rapidly increasing. With the increase of endoscope operations, related problems also emerged including the problems related to examinees of endoscope examination.

The problems related to examinees of endoscope examination are: first of all, the discomfort felt by the examinees due thick lines at the end of the connecting portion that enters the body; second, the pain felt by the examinees as the end portion of the endoscope is bent by manipulation by the examiner, irritating the inner walls of organs; third, secondary infection caused by endoscopes not cleaned or sterilized properly before entering human body; and fourth, the continuous pain felt by the examinee as the time that the endoscope remains inside the human body gets longer for the examiner to observe more parts inside the body since the camera for observation only provides a narrow view.

Therefore, numerous researches and developments are being made in order to resolve the aforementioned problems.

SUMMARY

The purpose of the present disclosure is to resolve the aforementioned problems of related art, more particularly, to provide a multi-view and multi-focused imaging apparatus having an actively variable lens so that numerous images can be obtained from various viewpoints in a short period of time when taking images.

Another purpose of the present disclosure is to provide an image apparatus having a multi-view and multi-focused actively variable lens at an end portion thereof whereby there is no need to bend the end portion of the endoscope and thus making it possible to use a thinner connector for connecting the end portion of the endoscope and the controller.

In one general aspect, there is provided an imaging apparatus comprising: an end portion configured to take an image; a controller configured to control the end portion and process the image input by the end portion; and a connector configured to connect the end portion and the controller, wherein the end portion is provided with at least one lens apparatus surrounding an exterior surface of the end portion, the lens apparatus being adapted to be brought to various focuses.

In the general aspect of the imaging apparatus, the end portion may be provided such that it is successive with the connector.

In the general aspect of the imaging apparatus, the lens apparatus may further comprise a lens of which a curvature may be increased or decreased by electric signals being input from the controller.

In the general aspect of the imaging apparatus, the lens may be extended or compressed to both ends in proportion to an extent of the electric signals input.

In the general aspect of the imaging apparatus, the lens may be provided such that both ends thereof are connected to the exterior surface of the end portion.

In the general aspect of the imaging apparatus, the end portion may comprise at least one light source for shedding light on the image.

In the general aspect of the imaging apparatus, the at least one light sources may be provided between the at least one lens apparatuses.

In the general aspect of the imaging apparatus, the end portion may comprise a gas injector configured to inject gas for expanding any space.

In the general aspect of the imaging apparatus, the gas injector may penetrate the end portion.

In the general aspect of the imaging apparatus, the end portion may have a circular or oval cross-section.

In the general aspect of the imaging apparatus, the lens apparatus may comprise a lens configured to take the image; a lens supporter configured to support the lens; and an image sensor configured to extract the image taken by the lens.

In the general aspect of the imaging apparatus, the lens supporter may be provided in the exterior of the end portion, and may support the lens and the image sensor.

In the general aspect of the imaging apparatus, a curvature of the lens may be increased or decreased by electric signals input from the controller.

In the general aspect of the imaging apparatus, the lens may be extended or compressed to both ends in proportion to an extent of the electric signals input.

In the general aspect of the imaging apparatus, the controller may comprise a processing apparatus configured to process information obtained by the end portion, wherein the processing apparatus creates a three dimensional image by using the information.

An imaging apparatus according to the present disclosure is provided with a multi-view and multi-focused active variable lens, and thus has an effect of obtaining images from various viewpoints at a short period of time, and when used as an endoscope, the multi-view and multi-focused variable lens at the end portion thereof need not be moved, making it possible to reduce the thickness of the connector that connects the end portion of the endoscope with the controller.

Furthermore, when used as an endoscope, an imaging apparatus according to the present disclosure is capable of obtaining numerous images of various viewpoints in a short time without the need to direct the lens of the endoscope towards various directions, thereby significantly reducing the time the endoscope stays inside the body of the examinee and the discomfort the examinee has to feel.

By using taken images at a time, the examinee can be provided with a three dimensional image in a short time after or during the endoscopy.

Figure 1:
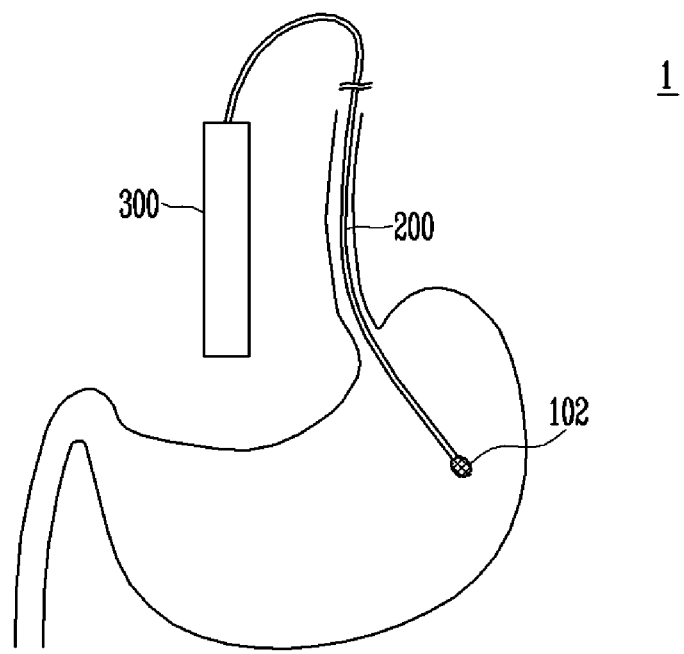
FIG. 1 is a conceptual diagram of an imaging apparatus according to an exemplary embodiment of the present disclosure.

Throughout the drawings and the detailed description, unless otherwise described, the same drawing reference numerals will be understood to refer to the same elements, features, and structures. The relative size and depiction of these elements may be exaggerated for clarity, illustrating, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the systems, apparatuses and/or methods described herein will be suggested to those of ordinary skill in the art. Also, descriptions of well-known functions and constructions may be omitted for increased clarity and conciseness.

Exemplary embodiments of the present disclosure will be explained in detail with reference to the drawings attached.

Figure 2:
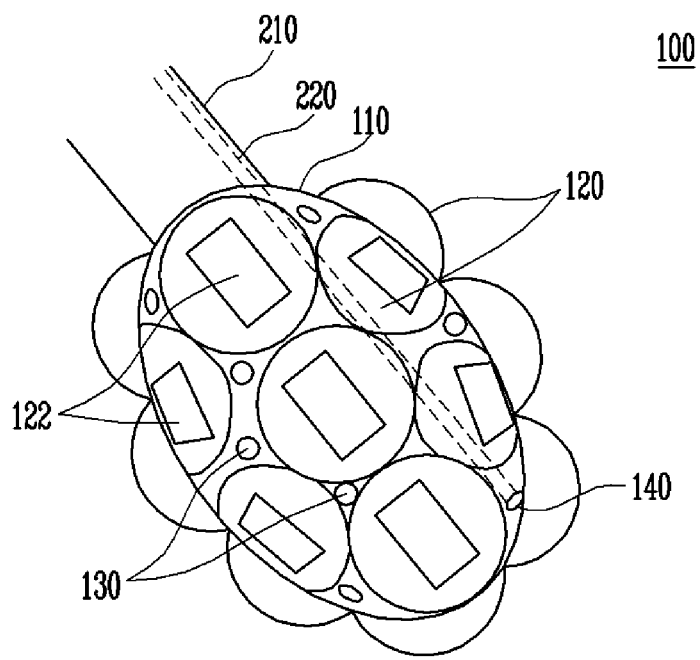
FIG. 2 is a conceptual diagram of an end portion of an imaging apparatus according to an exemplary embodiment of the present disclosure.
Figure 3:
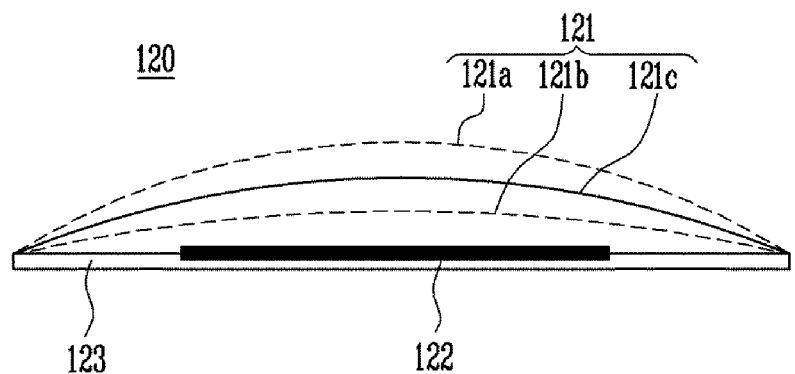
FIG. 3 is a conceptual diagram of a lens of an imaging apparatus according to an exemplary embodiment of the present disclosure.
Figure 4:
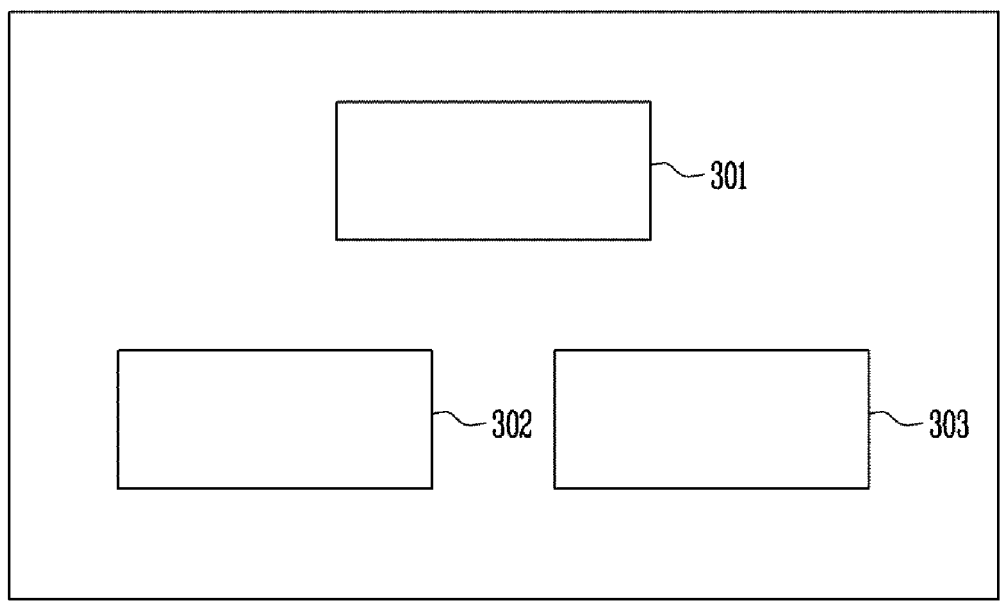
FIG. 4 is a conceptual diagram of a controller according to an exemplary embodiment of the present disclosure.

FIG. 1 is a conceptual diagram of an imaging apparatus according to an exemplary embodiment of the present disclosure, FIG. 2 is a conceptual diagram of an end portion of an imaging apparatus according to an exemplary embodiment of the present disclosure, FIG. 3 is a conceptual diagram of a lens of an imaging apparatus according to an exemplary embodiment of the present disclosure, and FIG. 4 is a conceptual diagram of a controller according to an exemplary embodiment of the present disclosure.

As illustrated in FIGS. 1 to 4, an imaging apparatus 1 comprises an end portion 100, connector 200, and controller 300. The imaging apparatus 1 according to exemplary embodiments of the present disclosure may be used as an internal imaging apparatus (not illustrated), but it may preferably be applied to an endoscope (not illustrated).

The end portion 100 observes various objects (not illustrated) and takes images. The images may be images of various external objects (not illustrated), and more preferably, the images may be images of the internal appearance of various objects (for example, inner wall of human organs (not illustrated)).

More specifically, the end portion 100 has a base 110, and it may comprise a lens apparatus 120 which may be brought into various focuses. Furthermore, in order to observe various objects properly, the end portion 100 may further comprise a light source 130 for shedding light on various objects, and also a gas injector 140 for injecting gas to expand a space.

The base 110 may comprise both the exterior and interior of the end portion 100, and it may also comprise apparatuses necessary for driving various apparatuses (not illustrated) that the end portion 100 comprises.

The lens apparatus 120 may comprise a lens 121 for taking an image, an image sensor 122 for extracting an image taken by the lens 121, and a lens supporter 123 for supporting the lens 121.

The curvature of the lens 121 may be increased or decreased by electric signals input from the controller 300 that will be explained hereinafter, and it may be extended or compressed to both ends in proportion to the extent the electric signals are input.

The lens 121 being extended or compressed to both ends changes the curvature changes thereby changing the focus of the lens 121. Therefore, the lens 121 may obtain an image of a long distance or short distance object based on focus change by changing of the curvature of the lens 121 even without having to move to the position to obtain the image.

The lens 121 may be automatically brought into focus by active changes in the curvature caused by electric signals. The lens 121 may be a morphing lens. More particularly, when extended to both ends by electric signals, the lens 121 may become lens when expanded 121a, whereby the focus is changed. Or, the lens 121 may be compressed to both ends and become lens when compressed 121b, whereby the focus is changed. When there is no electric signal, the lens may be lens in a normal mode 121c.

As such, the lens 121 may be extended or compressed by electric signals, thereby actively adjusting to be brought into a desired focus.

The lens 121 may be adapted such that both ends thereof are connected to an exterior surface of the end portion 100 (preferably to the base 100). Thus, the lens 121 may be adapted such that it surrounds the exterior surface of the end portion 110, providing an effect of taking multi-focused images.

The image sensor 122 may extract an image taken by the lens 121 as electric signals, and transmit the extracted signals to the controller 300. The image sensor 122 may extract the image obtained by the lens 121 as a high-definition image.

The image sensor 122 may obtain the multi-view and multi-focused images obtained by the lens 121 in a short period of time and extract the images as a high-definition image, and thus the image sensor 122 may make 3D images of an external object by combining the extracted numerous images.

The image sensor 122 may be a solid image sensor, more particularly, a metal oxide semiconductor (MOS) or a charge-coupled device (CCD). Of course, the image sensor 122 may convert an invisible image of an ultraviolet ray region that cannot be seen by human eyes into a visible image.

The lens supporter 123 may be provided in the exterior surface of the end portion 100 and support the lens 121 and image sensor 122. The lens supporter 123 may support both ends of the lens 121, and the lens supporter 123 may have the image sensor 122 between itself and the lens 121.

The lens supporter 123 may be of a flexible material so that it can be provided in the exterior surface of the end portion. It may be provided in an integral form and surrounding the exterior surface of the end portion 100, or be provided in a modular form so that a plurality of them can be connected, thereby surrounding the exterior surface of the end portion 100.

The lens apparatus 120 according to exemplary embodiments of the present disclosure is configured to surround the exterior surface of the end portion 100, and thus it may obtain three dimensional or multi-view images in a short period time, and change the curvature of the lens 121 by electric signals and obtain multi-focused images.

Therefore, the lens apparatus 120 is capable of obtaining three dimentional, multi-view and multi-focused images in a short period of time, thereby providing an effect of obtaining images without having to move the imaging apparatus 1, and also an effect of reducing the time needed for scanning an external object in order to obtain images.

Accordingly, when using an imaging apparatus 1 as an endoscope according to exemplary embodiments of the present disclosure, images may be obtained without having to move the imaging apparatus 1, and thus it is possible to significantly reduce pain to an examinee by irritating inside the body, and it is possible to obtain images of an observation object in a short period of time, thereby reducing the duration time of the irritation to the examinee as the endoscope goes inside the body. In other words, it is possible to significantly reduce the time of the endoscope moving inside the examinee, thereby playing a big role in reducing the pain to the examinee.

At least one light source 130 may be provided in the end portion 100, more particularly, between the lens apparatuses 120. The light source 130 used herein may be, but is not limited to, white light source or fluorescent light source.

The light source 130 may consist of white light source that sheds light on an external image to help the lens 121 take images effectively. The light source 130 may also consist of fluorescent light source that sheds blue light of any wavelength on a surface of an external image, amplifying the wavelength of the light being emitted and imaging the result, thereby obtaining various pieces of information that could not be obtained from white light source only.

The gas injector 140 may be configured at one side of the end portion while penetrating the end portion 100. The gas injector 140 may supply gas to form a space outside. The gas used in such a gas injector 140 may be for example, air.

The end portion 100 may be formed such that it is successive with the connector 200 that will be explained hereinafter. With an imaging apparatus 1 according to exemplary embodiments of the present disclosure, there is no need to bend the end portion 100 when taking images, and thus the imaging apparatus 1 may be formed such that it is successive with the connector 200, thereby saving the space occupied by the end portion 100 and accordingly providing an effect of further miniaturizing the imaging apparatus 1.

The end portion 100 may have a circular or oval cross-section. An imaging apparatus 1 according to exemplary embodiments may have a circular or oval cross-section, such that the lens apparatus 120 may face all directions in the space where the end portion 100 is located. Accordingly, the lens apparatus 120 has an effect of taking three dimentional or multi-view images.

The connector 200 connects the end portion 100 and the controller 300. The connector 200 may comprise a connecting line 210 that connects the end portion 100 and the controller 300, and a gas tube 220 that connects the gas injector 140.

In addition, besides the gas tube 220, the connector 200 may comprise an electric power line (not illustrated) for driving various apparatuses provided in the end portion 100, an information transmission line (not illustrated) for transmitting or receiving information collected by various apparatuses provided in the end portion 100, and a control line (not illustrated; for example a line for transmitting electric signals necessary to actively move the lens 121 of the lens apparatus 120, and control line for driving the light source 130, and the like) for controlling various apparatuses provided in the end portion 100.

In an imaging apparatus 1 according to exemplary embodiments, since the lens apparatus 120 consists of multi-view and multi-focused lens, there is no need to have a bending apparatus (not illustrated) of the connector 200 for changing directions of the end portion 100, and it is possible to miniaturize the apparatus (not illustrated) for focusing the lens 121, thereby providing an effect of significantly reducing the thickness of the connector 200. Therefore, it is possible to significantly reduce the irritation that the examinee (not illustrated) feels as an endoscope is inserted into the body.

In addition, an imaging apparatus 1 according to exemplary embodiments of the present disclosure being used as an endoscope may also comprise the configuration of a connector provided in a general endoscope. However, the connector provided in a general endoscope is just an example for explaining an imaging apparatus 1 according to exemplary embodiments of the present disclosure, and is similar to connectors used in general imaging apparatuses, and thus detailed explanation thereto is omitted.

The controller 300 controls the end portion 100 and processes the image input by the end portion 100. In addition, the controller 300 may comprise a control apparatus 301 for controlling various apparatuses included in the end portion 100 (for example, including, but is not limited to, lens apparatus 120, light source 130, gas injector 140, that is various apparatuses that may be mounted onto the end portion 100), a processing apparatus 302 for processing various information obtained by various apparatuses, and an electric apparatus 303 that supplies electric power for driving various apparatuses.

The processing apparatus 302 may receive 2D information, such as 2D image information or distance information from the end portion 100 to a target, from various devices provided in the end portion 100, and create a 3D image by using the 2D information through a 3D synthesis algorithm.

A detailed description of the 3D synthesis is omitted since it is substantially similar to the general 3D synthesis.

An examiner (not illustrated) is able to check the 3D synthetic data when the imaging apparatus 1 is inserted into the body and the imaging apparatus 1 is removed from the body.

The controller 300 may obviate an apparatus (not illustrated; for example, a lathe dog for bending the end portion 100 and the like) for moving the end portion 100, thereby maximizing miniaturization of an imaging apparatus 1 according to exemplary embodiments of the present disclosure.

However, the controller 300 of an imaging apparatus 1 according to exemplary embodiments of the present disclosure is similar to a controller for controlling a general imaging apparatus, and thus detailed explanation thereof is omitted.

As such, an imaging apparatus 1 according to exemplary embodiments of the present disclosure has a multi-view and multi-focused active variable lens 121, and thus provides an effect of obtaining numerous images of various viewpoints at a short period of time, and when used as an endoscope (not illustrated), the multi-view and multi-focused active variable lens 121 in the end portion 100 obviates the need to move the end portion 100 of the endoscope, thereby providing an effect of reducing the thickness of the connector 200 that connects the end portion 100 of the endoscope and the controller 300.

Furthermore, an imaging apparatus 1 according to the present disclosure, when used as an endoscope, may obtain numerous images of various viewpoints in a short period of time without having to make the lens of the endoscope face numerous directions, thereby providing an effect of effectively reducing the time it stays inside the body of the examinee and thus reducing the feeling of irritation to the examinee.

Although a few embodiments of the present invention have been shown and described, it would be appreciated by those skilled in the art that changes may be made in this embodiment without departing from the principles and spirit of the invention, the scope of which is defined in the claims and their equivalents.

What is claimed is:

1. An imaging apparatus comprising:
   an end portion configured to take an image of a subject;
   a controller configured to control the end portion and process the image input by the end portion; and
   a connector including a connecting line which connects the end portion and the controller,
   wherein a width of the connector is smaller than a central width of the end portion in a width direction of the connector,
   wherein the end portion is provided with at least one lens apparatus surrounding an exterior surface of the end portion, the lens apparatus being adapted to be brought to various focuses,
   wherein the end portion is shaped such that the exterior surface of the end portion includes a curved rear surface which faces the connecting line and a rear of the end portion, and a curved front surface opposite to the rear curved surface, which faces a front of the end portion, and the lens apparatus includes at least one rear lens apparatus disposed on the curved rear surface and at least one front lens apparatus disposed on the curved front surface, the curved rear surface being in contact with the connecting line, and
   wherein the lens apparatus comprises a lens of which a curvature increases or decreases by electric signals from the controller, such that a length of a curved periphery of a side-view of the lens between two points of the lens on a circumference of the lens which are on a diameter of the lens increases or decreases in proportion to an extent of the electric signals while a distance between said two points of the lens is maintained.

2. The imaging apparatus according to claim 1,
   wherein the end portion is provided such that it is successive with the connector.

3. The imaging apparatus according to claim 1,
   wherein the end portion comprises at least one light source for shedding light on the subject.

4. The imaging apparatus according to claim 3,
   wherein the at least one light source are provided between the at least one lens apparatuses.

5. The imaging apparatus according to claim 1,
   wherein the end portion comprises a gas injector configured to inject gas for expanding any space.

6. The imaging apparatus according to claim 5,
   wherein the gas injector penetrates the end portion.

7. The imaging apparatus according to claim 1,
   wherein the end portion has a circular or oval cross-section.

8. The imaging apparatus according to claim 1,
   wherein the lens apparatus further comprises
   a lens supporter configured to support the lens; and
   an image sensor configured to extract the image taken by the lens.

9. The imaging apparatus according to claim 8,
   wherein the lens supporter is provided in the exterior of the end portion, and supports the lens and the image sensor.

10. The imaging apparatus according to claim 1,
    wherein the controller comprises a processing apparatus configured to process information obtained by the end portion,
    wherein the processing apparatus creates a three dimensional image by using the information.

11. The imaging apparatus according to claim 1, wherein:
    the lens supporter is provided on the exterior surface of the end portion, to support the lens and the image sensor;
    said two points of the lens are connected to the lens supporter at two corresponding spots of the lens supporter; and
    a distance between the two spots of the lens supporter is maintained while the lens increases or decreases the curvature.

12. The imaging apparatus according to claim 11, wherein the lens supporter is provided such that a plurality of lens supporters are connected with each other and surround the exterior surface of the end portion.

13. An imaging apparatus comprising:
    an end portion configured to take an image;
    a controller configured to control the end portion and process the image input by the end portion; and
    a connector including a connector line which connects the end portion and the controller,
    wherein a width of the connector is smaller than a central width of the end portion in a width direction of the connector,
    wherein the end portion is provided with at least one lens apparatus surrounding an exterior surface of the end portion, the lens apparatus being adapted to be brought to various focuses,
    wherein the end portion is shaped such that the exterior surface of the end portion includes a curved rear surface which faces the connecting line and a rear of the end portion, and a curved front surface opposite to the rear curved surface, which faces a front of the end portion, and the lens apparatus includes at least one rear lens apparatus disposed on the curved rear surface and at least one front lens apparatus disposed on the curved front surface, the curved rear surface being in contact with the connecting line, and
    wherein the lens apparatus includes:
    a lens;
    a lens supporter provided on an exterior surface of the end portion, and supporting the lens such that, when the lens is taken from a side-view, two points of the lens on a circumference of the lens which are on a diameter of the lens are connected to the lens supporter at two corresponding spots of the lens supporter; and an image sensor supported by the lens supporter, wherein the lens supporter, taken from the side-view of the lens, extends without discontinuity between the two corresponding spots, and the image sensor is disposed on an upper surface of the lens supporter extending without discontinuity between the two corresponding spots.

14. The imaging apparatus according to claim 13, wherein the lens supporter is provided such that a plurality of lens supporters are connected with each other and surround the exterior surface of the end portion.

15. The imaging apparatus according to claim 1, wherein the end portion has a shape of an ovoid.

* * * * *